United States Patent
Abe et al.

(10) Patent No.: US 7,037,412 B2
(45) Date of Patent: May 2, 2006

(54) METHOD FOR PREPARING DEODORIZED N-VINYL-2-PYRROLIDONE

(75) Inventors: Kazuaki Abe, Osaka-fu (JP); Takashi Yodoshi, Kanagawa-ken (JP); Hitoshi Yano, Osaka-fu (JP)

(73) Assignee: Nippon Shokubai Co., Ltd., Osaka (JP)

(*) Notice: Subject to any disclaimer, the term of this patent is extended or adjusted under 35 U.S.C. 154(b) by 40 days.

(21) Appl. No.: 10/368,411

(22) Filed: Feb. 20, 2003

(65) Prior Publication Data

US 2003/0176712 A1    Sep. 18, 2003

(30) Foreign Application Priority Data

Feb. 20, 2002 (JP) .............................. 2002-043111
Feb. 20, 2002 (JP) .............................. 2002-043174

(51) Int. Cl.
*B01D 3/34* (2006.01)
*C07D 207/267* (2006.01)

(52) U.S. Cl. .............................. 203/6; 203/60; 203/62; 203/63; 203/67; 203/68; 203/69; 203/70; 203/71; 548/555

(58) Field of Classification Search ............ 203/6, 203/60, 62–63, 67–71, 85, 95–96; 548/552, 548/543, 555

See application file for complete search history.

(56) References Cited

U.S. PATENT DOCUMENTS

| 2,669,570 | A  | * | 2/1954  | Schnizer ..................... 548/552 |
| 2,775,599 | A  | * | 12/1956 | Pueter et al. ............... 548/552 |
| 4,415,468 | A  | * | 11/1983 | Chen et al. ................. 548/543 |
| 5,461,159 | A  | * | 10/1995 | Huckestein et al. ........ 548/555 |
| 6,436,243 | B1 | * | 8/2002  | Yamaguchi et al. .......... 203/71 |
| 6,726,811 | B1 | * | 4/2004  | Ugamura et al. ............. 203/74 |

FOREIGN PATENT DOCUMENTS

| EP | 1 094 061 | * | 4/2001  |
| GB | 717799    | * | 11/1954 |
| GB | 846575    | * | 8/1960  |

* cited by examiner

*Primary Examiner*—Virginia Manoharan
(74) *Attorney, Agent, or Firm*—Sherman & Associates

(57) ABSTRACT

The invention provides a method for producing purified N-vinyl-2-pyrrolidone free of odorous components. The method is composed of distilling with a distillation column a liquid, which is formed by adding to an odorous components-containing liquid having a N-vinyl-2-pyrrolidone purity of not lower than 90 wt %, a compound having boiling point lower than that of N-vinyl-2-pyrrolidone, and whereby removing the odorous components together with said low-temperature boiling compound as the distillate.

3 Claims, 3 Drawing Sheets

METHOD FOR PREPARING DEODORIZED N-VINYL-2-PYRROLIDONE

TECHNICAL FIELD TO WHICH THE INVENTION PERTAINS

This invention relates to a method for deodorization of N-vinyl-2-pyrrolidone, i.e., a method for preparing deodorized N-vinyl-2-pyrrolidone. N-vinyl-2-pyrrolidone is a compound useful as the starting monomer of poly(N-vinyl-2-pyrrolidone) which has a very broad spectrum of utility as a starting material of medicines, food additives and personal care products.

PRIOR ART

N-vinyl-2-pyrrolidone has been industrially manufactured by Reppe process wherein 2-pyrrolidone and acetylene are reacted in a liquid phase under elevated pressure in the presence of an alkali catalyst. There have been also proposed processes for preparing N-vinyl-2-pyrrolidone without using acetylene, for example, a process comprising reacting N-(2-hydroxyethyl)-2-pyrrolidone with thionyl chloride and dehydrochlorinating the resulting N-(2-chloroethyl)-2-pyrrolidone (U.S. Pat. No. 2,775,599), a process comprising reacting N-(2-hydroxyethyl)-2-pyrrolidone with acetic anhydride and removing acetic acid from the resulting acetic ester intermediate, or a process comprising subjecting N-(2-hydroxyethyl)-2-pyrrolidone to intramolecular dehydration reaction at vapor phase, in the presence of a catalyst (U.S. Pat. No. 5,625,076).

Because products of those processes contain, besides N-vinyl-2-pyrrolidone, unreacted starting materials, catalyst, by-products and the like, purified N-vinyl-2-pyrrolidone must be recovered by an adequate means, such as distillation or the like.

Such purified N-vinyl-2-pyrrolidone obtained by generally practiced recovery methods still contain, as disclosed in U.S. Pat. No. 5,329,021 or U.S. Pat. No. 5,710,284, impurities such as unsaturated hydrocarbons, basic compounds, vinyl ether compounds and the like which are side-products. These impurities not only are undesirable for such usages of the products as pharmaceuticals and food additives, but also adversely affect colors or odors of the products.

As means for solving above problem, for example, U.S. Pat. No. 5,039,817 discloses a process for removing the impurities with acidic ion exchanger, and U.S. Pat. No. 5,461,159 a process for treating the purified N-vinyl-2-pyrrolidone by adding thereto acid anhydride. These processes, however, additionally require regeneration of ion exchanger, use of auxiliary starting materials and their disposal, and hence are not commercially advantageous. U.S. Pat. No. 5,329,021 and U.S. Pat. No. 5,710,284 teach purification of said purified N-vinyl-2-pyrrolidone by means of multi-stage fractional crystallization. This method, however, is subject to the drawbacks that it requires a special apparatus, is complex in its steps and involves complicated operations.

PROBLEM TO BE SOLVED BY THE INVENTION

Accordingly, the object of the present invention is to provide a method for improving the drawbacks in the conventional art. More specifically, a method which enables to obtain purified N-vinyl-2-pyrrolidone free of the odorous components, from a liquid whose N-vinyl-2-pyrrolidone purity is at least 90 wt % and which contains the odorous components.

The above object of the present invention is accomplished by a method which comprises distilling with a distillation column a liquid which is formed by adding to said liquid having a N-vinyl-2-pyrrolidone purity of at least 90 wt % and containing odorous components, at least one compound having a boiling point lower than that of N-vinyl-2-pyrrolidone, and removing the odorous components together with the added compound(s) as the distillate.

WORKING EMBODIMENTS OF THE INVENTION

Hereinafter the invention is explained more specifically, in which NVP is an abbreviation for N-vinyl-2-pyrrolidone.

NVP-containing liquid recovered through conventional recovery means, which contains impurities such as unsaturated hydrocarbons, basic compounds, vinyl ethers and the like, in particular, odorous components, and has a NVP purity of not lower than 90 wt %, is the object (starting material) to be distilled according to the method of this invention. As examples of such NVP, those industrially produced by Reppe process, and those obtained by purifying the reaction products of the NVP production method disclosed in U.S. Pat. No. 5,625,076 until their NVP purity reaches 90 wt % or higher can be named.

The distillation operation according to the present invention is conducted under the following conditions. The operation can be practiced repeatedly, for increasing the deodorization effect.

Temperature of the bottom liquid is regulated to not higher than 180° C., preferably not higher than 165° C. When the bottom liquid temperature exceeds 180° C., polymerization or thermal decomposition of the NVP which is contained in the bottom liquid are promoted to reduce the NVP recovery ratio.

Operative pressure of the distillation column is usually not higher than $2.67 \times 10^4$ Pa (200 mmHg), preferably not higher than $2.00 \times 10^4$ Pa (150 mmHg), while it depends to some extent on the composition of the liquid to be distilled.

Distillation format is subject to no specific limitation, which may be either continuous type or batchwise distillation. The construction or form of the distillation column is again subject to no specific limitation and usually a rectification column such as a plate tower or packing tower is used. The number of plates in such a tower can be suitably selected according to the composition of the liquid to be distilled or reflux ratio, while usually the number of theoretical plates is in the order of 3–30.

In case of batchwise distillation, addition of a compound or compounds having a boiling point lower than that of NVP to the odorous components-containing liquid having a NVP purity of not lower than 90 wt % can be usually effected by such methods as: mixing the odorous components-containing liquid having a NVP purity of not lower than 90 wt % with a compound or compounds having a boiling point lower than that of NVP in advance and feeding the resulting solution into the column bottom, or feeding said two components separately into the column bottom. The methods of addition are not limited to the foregoing.

In case of the continuous distillation, location of entrance(s) for the liquid to be distilled is not subject to any specific limitation, but the liquid can be fed into the column through any desired site(s) in the distillation column. Nor the means for feeding the distillation liquid is subject to any particular limitation, while in normal practice a mixed solution of such an odorous components-containing liquid having a NVP purity of not lower than 90 wt % with a compound(s) having a boiling point lower than that of NVP is fed; or said two components may be fed separately. Method of adding the compound(s) having boiling point lower than that of NVP again is not subject to any specific limitation. The odorous components-containing liquid of not lower than 90 wt % in NVP purity and the compound(s) may be mixed in advance, or they may be continuously mixed (supplied while being mixed).

As stated earlier, the reaction products according to the NVP producing method as disclosed in U.S. Pat. No. 5,625,076, which are subsequently purified until the NVP purity reaches not lower than 90 wt %, are useful as the starting material of the present method invention. According to the method of U.S. Pat. No. 5,625,076, a reaction product comprising NVP, N-(2-hydroxyethyl)-2-pyrrolidone (abbreviated as HEP), compounds other than HEP, having boiling points higher than that of NVP (e.g., 2-pyrrolidone, NVP dimer and the like), water and the odorous components (The reaction product is hereafter referred to as "the crude liquid".) is formed through vaporous intramolecular dehydration reaction of N-(2-hydroxyethyl)-2-pyrrolidone in the presence of specific catalyst. When the crude liquid is distilled (first stage distillation) to distill water off from the column top, and the recovered bottom liquid (dehydrated liquid) is distilled (second stage distillation), the NVP of not lower than 90 wt % in purity which is useful as the starting material of the present method invention is obtained from the column top as the distillate. Details of the procedures for preparing NVP of not lower than 90 wt % in purity are explained hereinbelow.

The distillation (first stage distillation) for preparing the dehydrated liquid from the crude liquid is conducted under the following conditions.

Temperature of the bottom liquid is regulated to not higher than 180° C., preferably not higher than 165° C. Where the bottom liquid temperature is higher than 180° C., polymerization or thermal decomposition of the NVP contained in the bottom liquid are promoted to reduce the recovery ratio of the NVP.

The operating pressure in the distillation column is normally not higher than $2.67 \times 10^4$ Pa (200 mmHg), preferably not higher than $2.00 \times 10^4$ Pa (150 mmHg), while it depends to some extent on composition of the liquid to be distilled.

Distillation format is subject to no specific limitation, which may be either continuous or batchwise distillation.

Distillation (second stage distillation) of the dehydrated liquid is conducted under the following conditions.

The bottom liquid temperature is not higher than 230° C., preferably not higher than 210° C. Where the bottom liquid temperature exceeds 230° C., risks for reduction in NPV recovery ratio due to its thermal polymerization or decomposition and for plate efficiency drop or column clogging due to deposition of the formed polymer increase.

The operating pressure in the distillation column depends to some extent on composition of the liquid to be distilled, while normally the operable pressure at the bottom liquid temperature not higher than 230° C., avoiding the above problems, is not higher than $1.33 \times 10^4$ Pa (100 mHg), preferably not higher than $0.67 \times 10^4$ Pa (50 mmHg).

The format of the distillation is subject to no particular limitation, and either continuous or batchwise distillation can be practiced.

Where the distillation is continuously conducted, the distillation liquid can be supplied from optional site of the distillation column.

The distillate from the second stage distillation is a starting material in the method of the present invention. Following the present invention, therefore, a compound or compounds having boiling point lower than that of NVP are added to this distillate, to be distilled together. This distillation (third stage distillation) is conducted under the conditions similar to those earlier stated, i.e., the bottom liquid temperature not higher than 180° C., preferably not higher than 165° C.; and the operating pressure not higher than $2.67 \times 10^4$ Pa (200 mmHg), preferably not higher than $2.00 \times 10^4$ Pa (150 mmHg).

Where necessary, the bottom liquid from the third stage distillation may be subjected to a fourth stage distillation to provide a still more purified NVP.

While the compounds having boiling points lower than that of NVP are not subject to any particular limitation, those containing hydroxyl groups or those boiling at temperatures not higher than 150° C. under normal pressure are preferred. Water is convenient, because it is easy of handling, economical and itself odorless. When a prescribed amount or more of a hydroxyl group-containing compound, e.g., water, is added to NVP, odor of NVP itself decreases due to the dilution, but our observation has revealed that the odor of the odorous components is smelt more distinctly (cf. later appearing "odor-sensing test"). This phenomenon is presumed to take place because water has higher affinity to NVP than those odorous components do. This is the reason why hydroxyl-containing compounds are preferred as the compounds having boiling points lower than that of NVP. The reason why those compounds having boiling points not higher than 150° C. under normal pressure are preferred lies in their easy separability by distillation.

As specific examples of the compounds having boiling points lower than that of NVP, the following may be named: aliphatic hydrocarbons such as pentane, hexane, cyclohexane, methylcyclohexane, heptane, octane and iso-octane; aromatic hydrocarbons such as benzene, toluene, xylene and ethylbenzene; halogenated hydrocarbons such as dichloromethane, 1,2-dichloroethane, chloroform, carbon tetrachloride and chlorobenzene; alcohol compounds such as methanol, ethanol, 1-propanol, 2-propanol, 1-butanol, 2-butanol, isobutanol and t-butanol; ether compounds such as diethyl ether, diisopropyl ether, dibutyl ether, tetrahydrofuran, dioxolane, dioxane, 1,2-dimethoxyethane and 1,2-diethoxyethane; ketone compounds such as acetone, methyl ethyl ketone and methyl isobutyl ketone; ester compounds such as methyl formate, ethyl formate, methyl acetate and ethyl acetate; and besides, water, acetonitrile, nitromethane and the like.

The amount of such compound(s) having boiling point lower than that of NVP to be added can range, based on the weight of the odorous components-containing-liquid in which the purity of NVP is not lower than 90 wt %, 0.03–1.0 time, preferably 0.05–0.7 time, inter alia, 0.1–0.5 time When the amount added is less than 0.03 time of the liquid, satisfactory removal of the odorous components by the distillation cannot be achieved. Whereas, when it is more than 1.0 time, enormous energy is consumed for the distillation, rendering the method economically disadvantageous.

It is also possible to achieve improvement in color, by repeating distillation of the bottom liquid according to the method of the present invention. In the present method, the deodorizing effect can also be achieved by subjecting the bottom liquid from the distillation column to generally practiced crystallization process. The general crystallization process herein referred to includes, for example, the processes as disclosed in *Kagakukogaku Binran* (handbook of chemical engineering) (6th revised edition, ed. by Chemical Engineering Association), pp. 505–512, such as batchwise crystallization process using, for example, cooling tank, flowing-down fluid film-type crystallizer (FFC); and continuous crystallization process using 4C crystallizer, KCP apparatus and the like, while not limited to these.

EXAMPLE

Hereinafter the present invention is more specifically explained, referring to working examples, a referential example and comparative examples.

Examples 1–3 are typical working examples of the method of this invention.

The referential example describes preparation of said crude liquid and dehydrated liquid.

Examples 4–6 illustrate working of the method of this invention, starting from the dehydrated liquid obtained in the referential example.

Comparative Examples show the cases of conducting the distillation without adding the compound(s) having boiling point lower than that of NVP.

Referring to the drawings.

EXAMPLE 1

Figure 1:
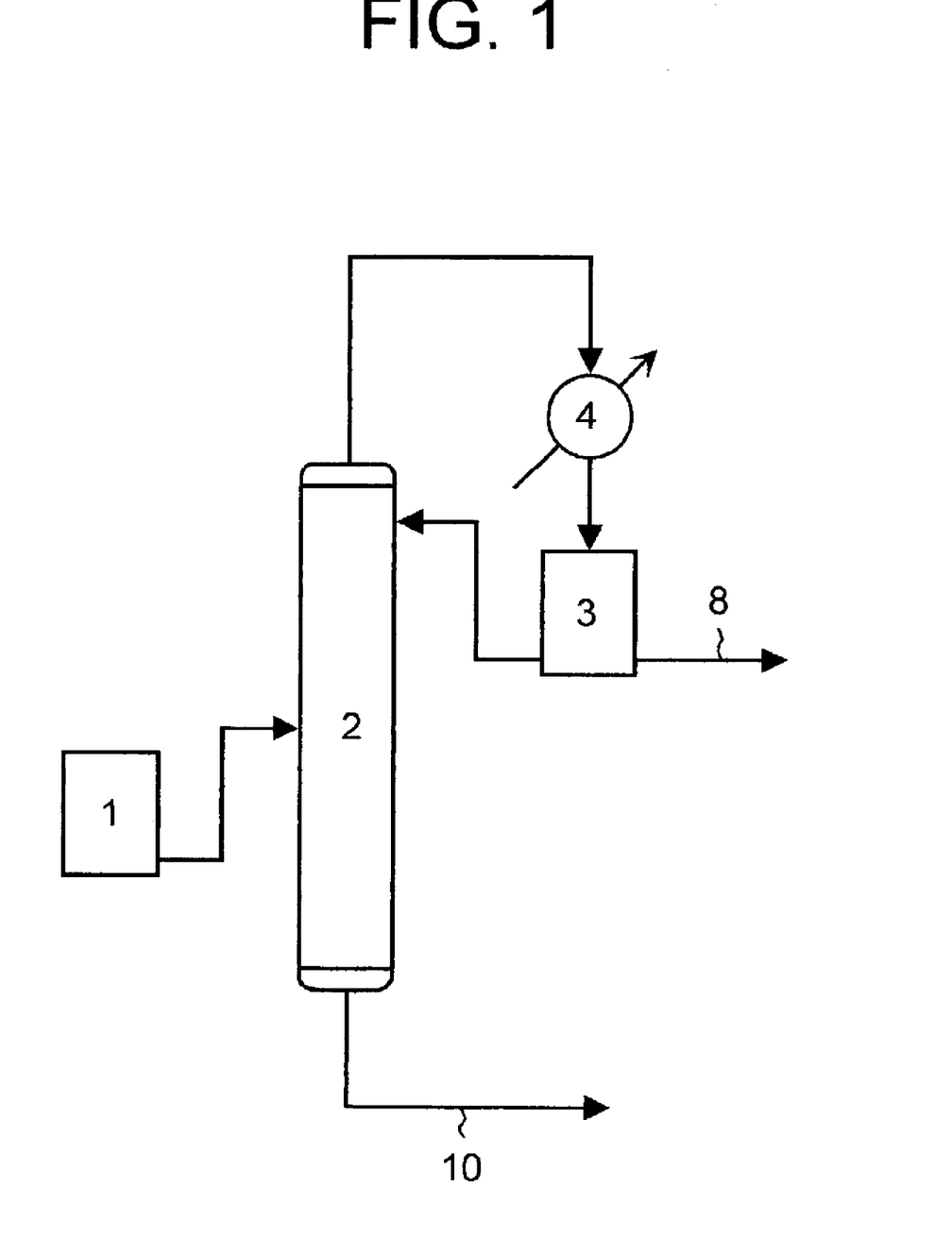
FIG. 1 is a block chart of the distillation apparatus which was used in Examples 1–3.

Using the apparatus as illustrated in FIG. 1, the method of the present invention was worked. A solution of a liquid containing an odorous components-containing N-vinyl-2-pyrrolidone of 99.8 wt % in purity in 0.33 wt time thereof of water was continuously distilled. As the continuous distillation column 2, a glass tube of 35 mm in inner diameter filled with 4 elements of stainless steel Sulzer packing of 35 mm in diameter in the condensing zone and 6 elements of identical packing in the recovering zone was used. The temperature of the distillate in the distillate tank 3 was maintained at 10° C. The continuous distillation column 2 was operated under a pressure of 1.33×10⁴ Pa (100 mmHg), and the flow rate of the distillate refluxed from the distillate tank 3 into the continuous distillation column 2 was so controlled as to make the reflux ratio 1 under said pressure. In FIG. 1, 4 is the condenser and 8 and 10 are conduits. The amount of the liquid supplied from the tank 1 to the continuous distillation column 2 per unit time (hereafter referred to as "supply rate"), amount of the distillate distilled off from the continuous distillation column 2 and withdrawn from the conduit 8 via the condenser 4 and distillate tank 3, per unit time ("distillation rate") and the amount of the bottom liquid withdrawn from the continuous distillation column 2 via the conduit 10, per unit time ("withdrawal rate of bottom liquid") and the compositions of the respective liquids were as shown in Table 1. In said Table 1, NVP signifies N-vinyl-2-pyrrolidone. The temperature at the top of the continuous distillation column 2 and that of the bottom liquid were as shown in Table 2.

TABLE 1

| | | Composition | |
|---|---|---|---|
| | | water (g/hr) | NVP (g/hr) |
| Continuous Distillation Column 2 | supply rate | 95.4 | 286.2 |
| | distillation rate | 95.4 | 0 |
| | withdrawal rate of bottom liquid | 0 | 286.2 |

TABLE 2

| | Continuous Distillation Column 2 |
|---|---|
| Column top temp. (° C.) | 53 |
| Bottom liquid temp. (° C.) | 154 |

We have been aware of the phenomenon that odor of the odorous components in N-vinyl-2-pyrrolidone is smelt more distinctly when odorous components-containing N-vinyl-2-pyrrolidone is diluted with a compound or compounds having hydroxyl groups, for example, water, of a prescribed amount or more, while the odor of the N-vinyl-2-pyrrolidone per se decreases. This phenomenon can be utilized for an odor-sensing test for N-vinyl-2-pyrrolidone. An example of the odor-sensing test for the odorous components-containing liquid of 99.8 wt % in NVP purity to be supplied to the continuous distillation column 2 (i.e., the feed liquid to the column 2) was conducted in the following manner. Ten subjects were let smell the feed liquid to the continuous distillation column 2 and 10 wt % aqueous solution thereof, and the numbers of the subjects who sensed the odor were recorded, with the result as shown in Table 3.

TABLE 3

| Sample | Number of subjects who sensed odor/Total number of subjects |
|---|---|
| Feed liquid to continuous distillation column 2 in Example 1 | 6/10 |
| 10% by weight aqueous solution thereof | 10/10 |

As demonstrated in above Table 3, odor is sensed more distinctly from solution diluted with water. Therefore, in the odor-sensing tests conducted in the following examples, 10% aqueous solutions of the liquids to be tested were used as the samples.

The result of the odor-sensing test of the bottom liquid of the continuous distillation column 2 is shown in Table 4.

TABLE 4

| Sample | Number of subjects who sensed odor/Total number of subjects |
|---|---|
| 10% by weight aqueous solution of bottom liquid from continuous distillation column 2 | 0/10 |

Purity of the N-vinyl-2-pyrrolidone from which the odorous components were removed in the described manner (i.e., the bottom liquid from the continuous distillation column 2) was 99.9 wt %.

EXAMPLE 2

Using the apparatus as illustrated in FIG. 1, the method of the present invention was worked. A mixed solution of a liquid containing an odorous components-containing N-vinyl-2-pyrrolidone of 99.8 wt % in purity with 0.33 wt % time thereof of methanol was continuously distilled. As the continuous distillation column 2, one of identical construction with the column used in Example 1 was used, and the temperature of the distillate in the distillate tank 3 was maintained at 10° C. The operation pressure of the column 2 was $1.33 \times 10^4$ Pa (100 mmHg) and the flow rate of the distillate refluxed from the distillate tank 3 into the continuous distillation column 2 was so controlled as to make the reflux ratio 0.5 under said pressure. The supply rate of the feed solution, distillation rate of the distillate and withdrawal rate of the bottom liquid, into or from the distillation column 2, and the compositions of the respective liquids were as shown concurrently in Table 5. In Table 5, NVP signifies N-vinyl-2-pyrrolidone. The temperature at the top of the continuous distillation column 2 and that of the bottom liquid were as shown in Table 6. Furthermore, the result of the odor-sensing test of the bottom liquid from the continuous distillation column 2 was as shown in Table 7.

TABLE 5

|  |  | Composition | |
| --- | --- | --- | --- |
|  |  | water (g/hr) | NVP (g/hr) |
| Continuous Distillation Column 2 | supply rate | 101.6 | 304.8 |
|  | distillation rate | 101.6 | 0 |
|  | withdrawal rate of bottom liquid | 0 | 304.8 |

TABLE 6

|  | Continuous Distillation Column 2 |
| --- | --- |
| Column top temp. (° C.) | 21 |
| Bottom liquid temp. (° C.) | 154 |

TABLE 7

| Sample | Number of subjects who sensed odor/Total number of subjects |
| --- | --- |
| 10 wt. % aqueous solution of bottom liquid from continuous distillation column 2 | 3/10 |

Purity of the N-vinyl-2-pyrrolidone (bottom liquid of the continuous distillation column 2) from which the odorous components were removed was 99.9 wt %.

EXAMPLE 3

Using the apparatus as illustrated in FIG. 1, the method of the present invention was worked. A mixed solution of a liquid containing an odorous components-containing N-vinyl-2-pyrrolidone of 99.8 wt % in purity with each 0.13 wt % time thereof of water and 1,2-dimethoxyethane was continuously distilled. As the continuous distillation column 2, one of identical construction with the column used in Example 1 was used, and the temperature of the distillate in the distillate tank 3 was maintained at 10° C. The operation pressure of the column 2 was $1.33 \times 10^4$ Pa (100 mmHg) and the flow rate of the distillate refluxed from the distillate tank 3 into the continuous distillation column 2 was so controlled as to make the reflux ratio 0.5 under said pressure. The supply rate of the feed solution, distillation rate of the distillate and withdrawal rate of the bottom liquid, into or from the distillation column 2, and the compositions of the respective liquids were as shown concurrently in Table 8. In Table 8, NVP signifies N-vinyl-2-pyrrolidone. The temperature at the top of the continuous distillation column 2 and that of the bottom liquid were as shown in Table 9. Furthermore, the result of the odor-sensing test of the bottom liquid from the continuous distillation column 2 was as shown in Table 10.

TABLE 8

|  |  | Composition | | |
| --- | --- | --- | --- | --- |
|  |  | water (g/hr) | 1,2-di-methoxyethane (g/hr) | NVP (g/hr) |
| Continuous distillation column 2 | supply rate | 39.3 | 39.3 | 314.1 |
|  | distillation rate | 39.3 | 39.3 | 0 |
|  | withdrawal rate of bottom liquid | 0 | 0 | 314.1 |

TABLE 9

|  | Continuous Distillation Column 2 |
| --- | --- |
| Column top temp. (° C.) | 49 |
| Bottom liquid temp. (° C.) | 154 |

TABLE 10

| Sample | Number of subjects who sensed odor/Total number of subjects |
| --- | --- |
| 10 wt. % aqueous solution of bottom liquid from continuous distillation column 2 | 1/10 |

Purity of the N-vinyl-2-pyrrolidone (bottom liquid of the continuous distillation column 2) from which the odorous components were removed was 99.9 wt %.

REFERENTIAL EXAMPLE (PREPARATION OF CRUDE LIQUID AND DEHYDRATED LIQUID)

Cesium carbonate was impregnated in spherical silica gel (5–10 mesh) and calcined in air at 800° C. to provide a catalyst of the composition expressed as $Cs_1Si_{100}$ in terms of the atomic ratio excepting oxygen. Five (5) ml of this catalyst was filled in a stainless steel reaction tube of 10 mm in inner diameter, and the reaction tube was immersed in a molten salt bath of 370° C. A feed gas of N-(2-hydroxyethyl)-2-pyrrolidone (HEP) which was diluted with nitrogen until the former's partial pressure became 76 mmHg was supplied into the reaction tube at the HEP's space velocity of 200 $h^{-1}$ and reacted under normal pressure. The resulting reaction gas excepting nitrogen was cooled and trapped. Thus collected liquid, i.e., crude liquid, contained N-vinyl- 2-pyrrolidone, HEP, compounds other than HEP which have boiling points higher than that of N-vinyl-2-pyrrolidone, water and the odorous components. A dehydrated liquid was prepared from this crude liquid, according to the following procedures.

Figure 2:
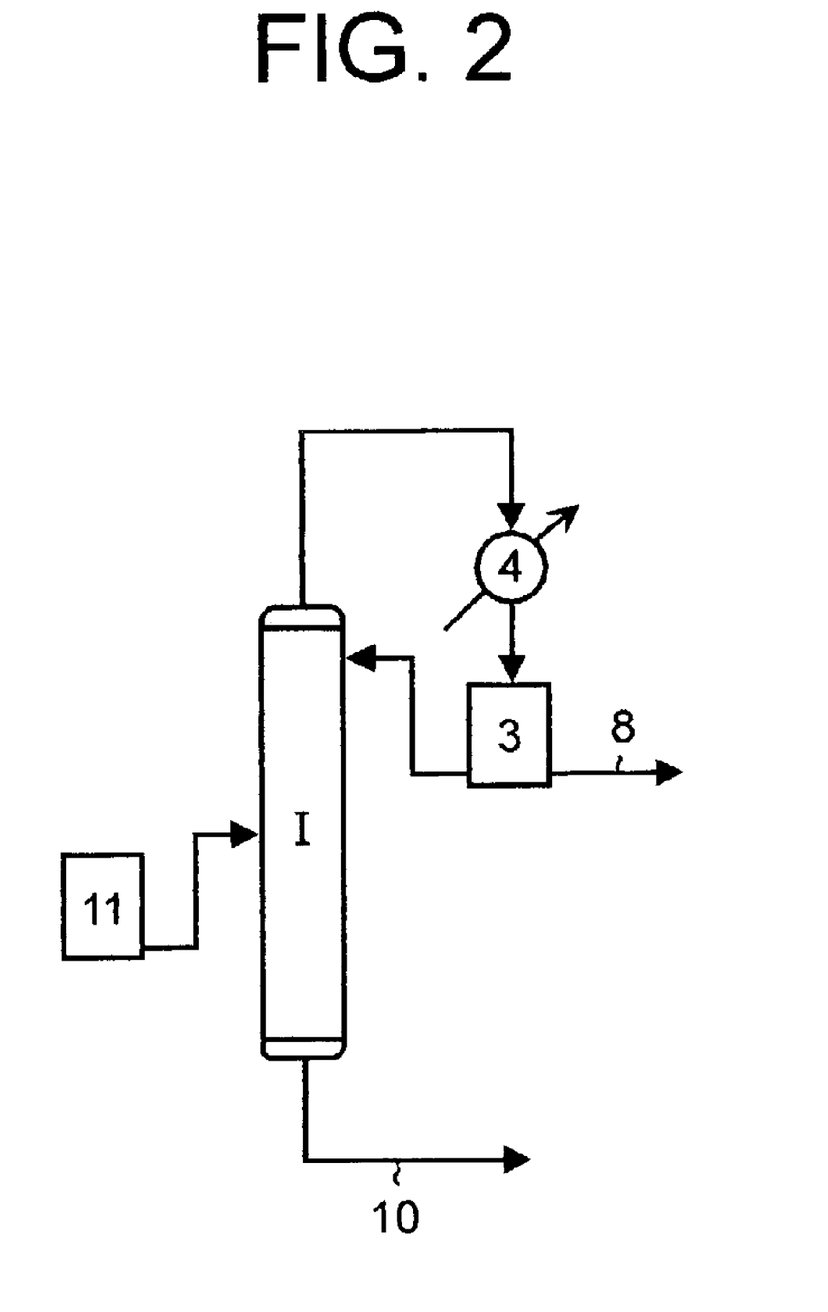
FIG. 2 is a block chart of the distillation apparatus which was used in the Referential Example for preparing the dehydrated liquid from the crude liquid.

Using the apparatus as illustrated in FIG. 2, the above crude liquid was continuously distilled. The crude liquid from the tank 11 was distilled at the continuous distillation column I (first stage distillation column). The water and odorous components were distilled off from the column top and discharged via the conduit 8, and a dehydrated liquid (bottom liquid) was obtained at the bottom of the column. As the continuous distillation column I, a glass tube of 35 mm in inner diameter filled with 4 elements of stainless steel Sulzer packing of 35 mm in diameter in the condensing zone and 6 elements of identical packing in the recovery zone was used. The temperature of the distillate in the distillate tank 3 was maintained at 10° C. The continuous distillation column I was operated under a pressure of $1.33 \times 10^4$ Pa (100 mmHg), and the flow rate of the distillate refluxed from the distillate tank 3 into the continuous distillation column I was so controlled as to make the reflux ratio 1 under said pressure. The supply rate to the continuous distillation column I, distillation rate and withdrawal rate of its bottom liquid, and the compositions of the respective liquids were as shown in Table 11. In Table 11, NVP stands for N-vinyl-2-pyrrolidone, HEP stands for N-(2-hydroxyethyl)-2-pyrrolidone, and high-temperature boiling compound means those compounds having boiling points higher than that of N-vinyl-2-pyrrolidone (excepting HEP). The column top temperature and the bottom liquid temperature of the continuous distillation column I were as shown in Table 12.

TABLE 11

| | | Composition | | | |
|---|---|---|---|---|---|
| | | water (g/hr) | NVP (g/hr) | HEP (g/hr) | High-temperature boiling compound (g/hr) |
| Continuous distillation column I | supply rate | 43.2 | 327.6 | 20.8 | 8.4 |
| | distillation rate | 43.2 | 0 | 0 | 0 |
| | withdrawal rate of bottom liquid | 0 | 321.8 | 20.8 | 14.2 |

TABLE 12

| | Continuous Distillation Column I |
|---|---|
| Column top temp. (° C.) | 53 |
| Bottom liquid temp. (° C.) | 159 |

EXAMPLE 4

Figure 3:
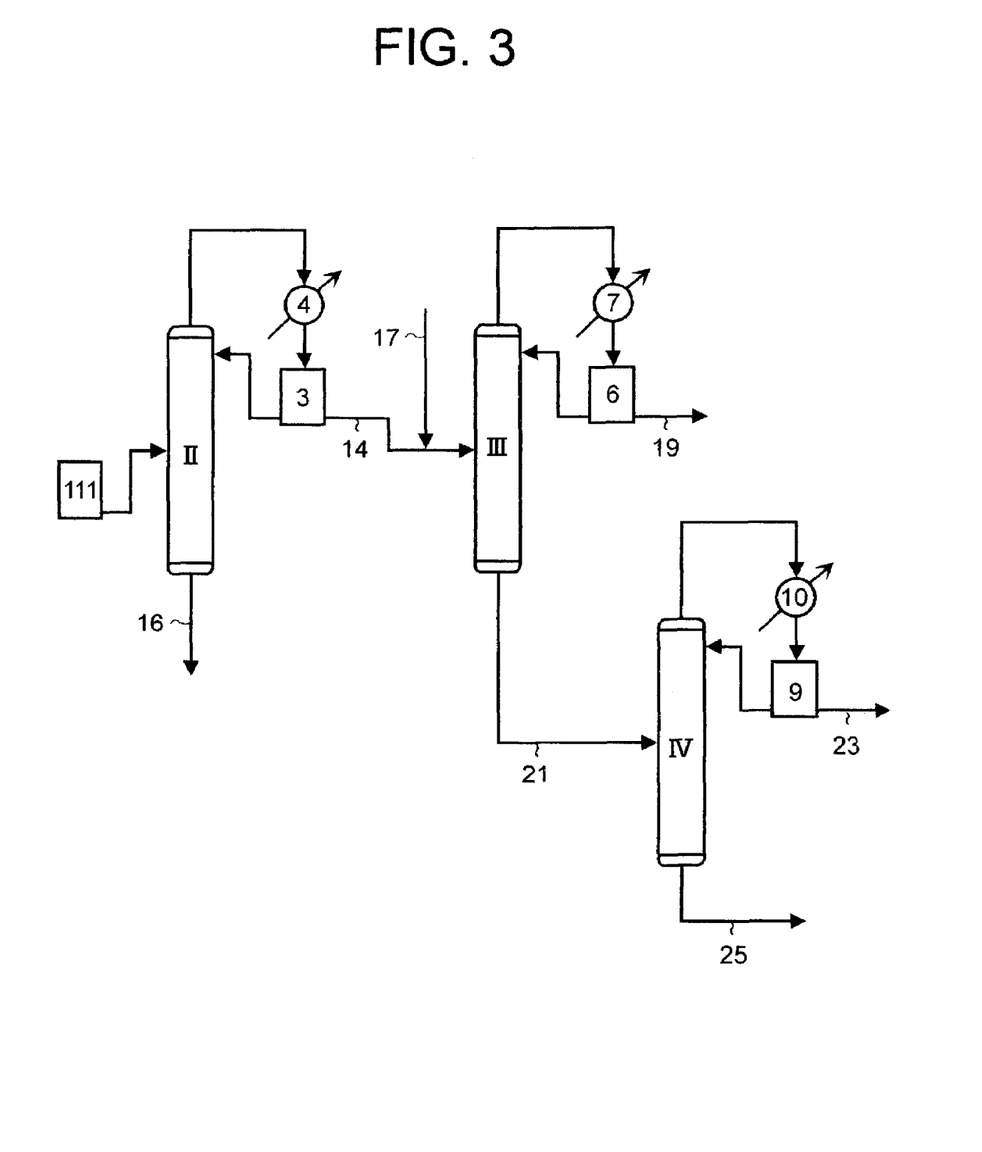
FIG. 3 is a block chart of the distillation apparatus which was used in Example 4–6.

Using the apparatus as illustrated in FIG. 3, the method of the present invention was worked. The bottom liquid (dehydrated liquid) as obtained in the Referential Example was continuously supplied from the tank 111 into the distillation column series and distilled. As the continuous distillation column II (second stage distillation column), a glass tube of 50 mm in inner diameter which was filled with 7 elements of stainless steel Sulzer packing of 50 mm in diameter in the condensing zone and 7 elements of identical packing in the recovering zone was used. As the continuous distillation column III (third stage distillation column), a glass tube of 35 mm in inner diameter which was filled with 4 elements of stainless steel Sulzer packing of 35 mm in diameter in the condensing zone and 6 elements of identical packing in the recovering zone was used. As the continuous distillation column IV (fourth stage distillation column), a glass tube of 50 mm in inner diameter, which was filled with 7 elements of stainless steel Sulzer packing of 50 mm in diameter in the condensing zone and 7 elements of identical packing in the recovering zone was used. The temperature of the distillate in the distillate tanks 3, 6 and 9 was maintained at 10° C. The continuous distillation column II was operated under a pressure of $1.33 \times 10^3$ Pa (10 mmHg) and the flow rate of the distillate which was refluxed from the distillate tank 3 into the continuous distillation column II was so controlled as to make the reflux ratio 1 under said pressure. The operation pressure of the continuous distillation column III was $1.33 \times 10^4$ Pa (100 mmHg) and the flow rate of the distillate refluxed from the distillate tank 6 into the continuous distillation column III was so controlled as to make the reflux ratio 1 under said pressure. The operation pressure of the column IV was $1.33 \times 10^3$ Pa (10 mmHg) and the flow rate of the distillate refluxed from the distillate tank 9 into the continuous distillation column IV was so controlled as to make the reflux ratio 1 under said pressure.

The result of the odor-sensing test with the distillate from the continuous distillation column II was as shown in Table 13. The N-vinyl-2-pyrrolidone in the distillate from the continuous distillation column II had a purity of 99.8 wt %.

TABLE 13

| Sample | Number of subjects who sensed odor/Total number of subjects |
|---|---|
| 10 wt. % aqueous solution of distillate from continuous distillation column II | 10/10 |

The distillate discharged from the continuous distillation column II through the conduit 14 was mixed with 0.33 wt time thereof of water supplied through the conduit 17, and the resulting solution was continuously supplied to the continuous distillation column III. The bottom liquid from said column III was supplied to the continuous distillation column IV via the conduit 21, and N-vinyl-2-pyrrolidone was obtained as the distillate from the top of the continuous distillation column IV, via the conduit 23. Referring to FIG. 3, 4, 7 and 10 are condensers, and 16, 19 and 25 are discharge pipes. Supply rates, distillation rates and withdrawal rates of bottom liquids into and from the continuous distillation columns II, III and IV, respectively, are shown in Table 14, concurrently with the composition of each liquid. In Table 14, NVP stands for N-vinyl-2-pyrrolidone, HEP, N-(2-hydroxyethyl)-2-pyrrolidone, and high temperature-boiling compounds, those compounds having boiling points higher than that of N-vinyl-2-pyrrolidone (excepting HEP). The respective column top temperatures and the bottom liquid temperatures in the continuous distillation columns II, III and IV were as shown in Table 15. Furthermore, the result of odor-sensing test with the distillate from the continuous distillation column IV was as shown in Table 16.

TABLE 14

| | | Composition | | | |
|---|---|---|---|---|---|
| | | water (g/hr) | NVP (g/hr) | HEP (g/hr) | High-temperature boiling compound (g/hr) |
| Continuous distillation column II | supply rate | 0 | 321.8 | 20.8 | 14.2 |
| | distillation rate | 0 | 317.0 | 0 | 0 |
| | withdrawal rate of bottom liquid | 0 | 0 | 20.8 | 19.0 |
| Continuous distillation column III | supply rate | 105.7 | 317.0 | 0 | 0 |
| | distillation rate | 105.7 | 0 | 0 | 0 |
| | withdrawal rate of bottom liquid | 0 | 313.8 | 0 | 3.2 |
| Continuous distillation column IV | supply rate | 0 | 313.8 | 0 | 3.2 |
| | distillation rate | 0 | 313.8 | 0 | 0 |
| | withdrawal rate of bottom liquid | 0 | 0 | 0 | 3.2 |

TABLE 15

| | Continuous Distillation Column II | Continuous Distillation Column III | Continuous Distillation Column IV |
|---|---|---|---|
| Column top temp. (° C.) | 92 | 52 | 91 |
| Bottom liquid temp. (° C.) | 194 | 153 | 128 |

TABLE 16

| Sample | Number of subjects who sensed odor/Total number of subjects |
|---|---|
| 10 wt. % aqueous solution of distillate from continuous distillation column IV | 0/10 |

The so purified N-vinyl-2-pyrrolidone (distillate from the continuous distillation column IV) had a purity of 99.9 wt %.

EXAMPLE 5

Using the apparatus as illustrated in FIG. 3, the method of the present invention was worked. The bottom liquid (dehydrated liquid) as obtained in the Referential Example was continuously distilled. The continuous distillation columns II, III and IV of same constructions to those as described in Example 4 were used, and the temperature of the distillates in the distillate tanks 3, 6 and 9 was maintained at 10° C. The continuous distillation column II was operated under a pressure of $1.33 \times 10^3$ Pa (10 mmHg) and the flow rate of the distillate which was refluxed from the distillate tank 3 into the continuous distillation column II was so controlled as to make the reflux ratio 1 under said pressure. The operation pressure of the continuous distillation column III was $1.33 \times 10^4$ Pa (100 mmHg) and the flow rate of the distillate refluxed from the distillate tank 6 into the continuous distillation column III was so controlled as to make the reflux ratio 0.5 under said pressure. The operation pressure of the column IV was $1.33 \times 10^3$ Pa (10 mmHg) and the flow rate of the distillate refluxed from the distillate tank 9 into the continuous distillation column IV was so controlled as to make the reflux ratio 1 under said pressure.

The result of the odor-sensing test with the distillate from the continuous distillation column II was as shown in Table 17. The N-vinyl-2-pyrrolidone in the distillate from the continuous distillation column II had a purity of 99.8 wt %.

TABLE 17

| Sample | Number of subjects who sensed odor/Total number of subjects |
|---|---|
| 10 wt. % aqueous solution of distillate from continuous distillation column II | 10/10 |

The distillate discharged from the continuous distillation column II through the conduit 14 was mixed with 0.43 wt time thereof of methanol supplied through the conduit 17, and the resulting solution was continuously supplied to the continuous distillation column III. The bottom liquid from said column III was supplied to the continuous distillation column IV via the conduit 21, and N-vinyl-2-pyrrolidone was obtained as the distillate from the top of the continuous distillation column IV, via the conduit 23.

Supply rates, distillation rates and withdrawal rates of bottom liquids into and from the continuous distillation columns II, III and IV, respectively, are shown in Table 18, concurrently with the composition of each liquid. In Table 18, NVP stands for N-vinyl-2-pyrrolidone, HEP, N-(2-hydroxyethyl)-2-pyrrolidone, and high temperature-boiling compounds, those compounds having boiling points higher than that of N-vinyl-2-pyrrolidone (excepting HEP). The respective column top temperatures and the bottom liquid temperatures in the continuous distillation columns II, III and IV were as shown in Table 19. Furthermore, the result of odor-sensing test with the distillate from the continuous distillation column IV was as shown in Table 20.

TABLE 18

| | | Composition | | | |
|---|---|---|---|---|---|
| | | methanol (g/hr) | NVP (g/hr) | HEP (g/hr) | High-temperature boiling compound (g/hr) |
| Continuous distillation column II | supply rate | 0 | 321.8 | 20.8 | 14.2 |
| | distillation rate | 0 | 317.0 | 0 | 0 |
| | withdrawal rate of bottom liquid | 0 | 0 | 20.8 | 19.0 |
| Continuous distillation column III | supply rate | 135.9 | 317.0 | 0 | 0 |
| | distillation rate | 135.9 | 0 | 0 | 0 |
| | withdrawal rate of bottom liquid | 0 | 311.3 | 0 | 5.7 |
| Continuous distillation column IV | supply rate | 0 | 311.3 | 0 | 5.7 |
| | distillation rate | 0 | 311.3 | 0 | 0 |
| | withdrawal rate of bottom liquid | 0 | 0 | 0 | 5.7 |

TABLE 19

|  | Continuous Distillation Column II | Continuous Distillation Column III | Continuous Distillation Column IV |
|---|---|---|---|
| Column top temp. (° C.) | 92 | 21 | 90 |
| Bottom liquid temp. (° C.) | 194 | 153 | 128 |

TABLE 20

| Sample | Number of subjects who sensed odor/Total number of subjects |
|---|---|
| 10 wt. % aqueous solution of distillate from continuous distillation column IV | 3/10 |

The so purified N-vinyl-2-pyrrolidone (distillate from the continuous distillation column IV) had a purity of 99.9 wt %.

EXAMPLE 6

Using the apparatus as illustrated in FIG. 3, the method of the present invention was worked. The bottom liquid (dehydrated liquid) as obtained in the Referential Example was continuously distilled. The continuous distillation columns II, III and IV of same constructions to those as described in Example 4 were used, and the temperature of the distillates in the distillate tanks 3, 6 and 9 was maintained at 10° C. The continuous distillation column II was operated under a pressure of $1.33 \times 10^3$ Pa (10 mmHg) and the flow rate of the distillate which was refluxed from the distillate tank 3 into the continuous distillation column II was so controlled as to make the reflux ratio 1 under said pressure. The operation pressure of the continuous distillation column III was $1.33 \times 10^4$ Pa (100 mmHg) and the flow rate of the distillate refluxed from the distillate tank 6 into the continuous distillation column III was so controlled as to make the reflux ratio 1 under said pressure. The operation pressure of the column IV was $1.33 \times 10^3$ Pa (10 mmHg) and the flow rate of the distillate refluxed from the distillate tank 9 into the continuous distillation column IV was so controlled as to make the reflux ratio 1 under said pressure.

The result of the odor-sensing test with the distillate from the continuous distillation column II was as shown in Table 21. The N-vinyl-2-pyrrolidone in the distillate from the continuous distillation column II had a purity of 99.8 wt %.

TABLE 21

| Sample | Number of subjects who sensed odor/Total number of subjects |
|---|---|
| 10 wt. % aqueous solution of distillate from continuous distillation column II | 10/10 |

The distillate discharged from the continuous distillation column II through the conduit 14 was mixed with 0.2 wt time thereof of water and 0.13 wt time of the distillate of 1,2-dimethoxyethane supplied through the conduit 17, and the resulting solution was continuously supplied to the continuous distillation column III. The bottom liquid from said column III was supplied to the continuous distillation column IV via the conduit 21, and N-vinyl-2-pyrrolidone was obtained as the distillate from the top of the continuous distillation column IV, via the conduit 23.

Supply rates, distillation rates and withdrawal rates of bottom liquids into and from the continuous distillation columns II, III and IV, respectively, are shown in Table 22, concurrently with the composition of each liquid. In Table 22, NVP stands for N-vinyl-2-pyrrolidone, HEP, N-(2-hydroxyethyl)-2-pyrrolidone, and high temperature-boiling compounds, those compounds having boiling points higher than that of N-vinyl-2-pyrrolidone (excepting HEP). The respective column top temperatures and bottom liquid temperatures in the continuous distillation columns II, III and IV were as shown in Table 23. Furthermore, the result of odor-sensing test with the distillate from the continuous distillation column IV was as shown in Table 24.

TABLE 22

|  |  | Composition | | | | |
|---|---|---|---|---|---|---|
|  |  | Water (g/hr) | 1,2-di-methoxy-ethane (g/hr) | NVP (g/hr) | HEP (g/hr) | High-temperature boiling compound (g/hr) |
| Continuous distillation column II | supply rate | 0 | 0 | 321.8 | 20.8 | 14.2 |
|  | distillation rate | 0 | 0 | 317.0 | 0 | 0 |
|  | withdrawal rate of bottom liquid | 0 | 0 | 0 | 20.8 | 19.0 |
| Continuous distillation column III | supply rate | 63.4 | 42.3 | 317.0 | 0 | 0 |
|  | distillation rate | 63.4 | 42.3 | 0 | 0 | 0 |
|  | withdrawal rate of bottom liquid | 0 | 0 | 310.3 | 0 | 6.7 |
| Continuous distillation column IV | supply rate | 0 | 0 | 310.3 | 0 | 6.7 |
|  | distillation rate | 0 | 0 | 310.3 | 0 | 0 |
|  | withdrawal rate of bottom liquid | 0 | 0 | 0 | 0 | 6.7 |

TABLE 23

|  | Continuous Distillation Column II | Continuous Distillation Column III | Continuous Distillation Column IV |
|---|---|---|---|
| Column top temp. (° C.) | 92 | 50 | 91 |
| Bottom liquid temp. (° C.) | 194 | 154 | 128 |

TABLE 24

| Sample | Number of subjects who sensed odor/Total number of subjects |
|---|---|
| 10 wt. % aqueous solution of distillate from continuous distillation column IV | 1/10 |

The so purified N-vinyl-2-pyrrolidone (distillate from the continuous distillation column IV) had a purity of 99.9 wt %.

COMPARATIVE EXAMPLE

The bottom liquid (dehydrated liquid) as obtained in the Referential Example was continuously distilled, using a distillation apparatus of a similar construction as illustrated in FIG. 2. Said distillation apparatus was same to the one used in the Referential Example, except that the continuous distillation column I was a glass tube of 50 mm in inner diameter which was filled with 7 elements of stainless steel Sulzer packing of 50 mm in diameter in its condensing zone and 7 elements of identical packing in its recovering zone. The temperature of the distillate in the distillate tank 3 was maintained at 10° C. The operation pressure of the column I was $1.33 \times 10^3$ Pa (10 mmHg), and the flow rate of the distillate refluxed from the distillate tank 3 into the column I was so controlled as to make the reflux ratio 1 under said pressure. The supply rate, distillation rate and withdrawal rate of the bottom liquid into or from the continuous distillation column I and the compositions of the respective liquids were as shown in Table 25. In Table 25, NVP stands for N-vinyl-2-pyrrolidone, HEP stands for N-(2-hydroxyethyl)-2-pyrrolidone and high-temperature boiling compound means those compounds having boiling points higher than that of N-vinyl-2-pyrrolidone (excepting HEP). The column top temperature and the bottom liquid temperature of the continuous distillation column I were as shown in Table 26. The result of the odor-sensing test with the distillate from the continuous distillation column I was, as indicated in Table 27, unfavorable.

TABLE 25

| | | Composition | | | |
|---|---|---|---|---|---|
| | | water (g/hr) | NVP (g/hr) | HEP (g/hr) | High-temperature boiling compound (g/hr) |
| Continuous distillation column I | supply rate | 0 | 321.8 | 20.8 | 14.2 |
| | distillation rate | 0 | 317.0 | 0 | 0 |
| | withdrawal rate of bottom liquid | 0 | 0 | 20.8 | 19.0 |

TABLE 26

| | Continuous Distillation Column I |
|---|---|
| Column top temp. (° C.) | 92 |
| Bottom liquid temp. (° C.) | 194 |

TABLE 27

| Sample | Number of subjects who sensed odor/Total number of subjects |
|---|---|
| 10 wt. % aqueous solution of the distillate from continuous distillation column I in Comparative Example | 10/10 |

The purity of the N-vinyl-2-pyrrolidone in the distillate from the continuous distillation column I was 99.8 wt %.

The invention claimed is:

1. A method for producing deodorized N-vinyl-2-pyrrolidone, said method comprising the step of distilling a liquid, which is formed by adding at least one compound having boiling point lower than that of N-vinyl-2-pyrrolidone to odorous components-containing liquid having a N-vinyl-2-pyrrolidone purity of not lower than 90% by weight, with a distillation column and whereby eliminating the odorous components with said compound as the distillate, wherein the compound having boiling points lower than that of N-vinyl-2pyrrolidone is selected from the group consisting of aliphatic hydrocarbons, aromatic hydrocarbons, halogenated hydrocarbons, alcohols, ethers, ketones, esters, acetonitrile and nitromethane.

2. A method according to claim 1, in which the compound having a boiling point lower than that of N-vinyl-2-pyrrolidone is a compound containing hydroxyl groups or having a boiling point not higher than 150° C. under normal pressure.

3. A method according to claim 2, in which the compound having a boiling point lower than that of N-vinyl-2-pyrrolidone is methanol or 1,2-dimethoxyethane.

* * * * *